(12) United States Patent
Bencini

(10) Patent No.: US 11,684,416 B2
(45) Date of Patent: Jun. 27, 2023

(54) INSULATED ABLATION CATHETER DEVICES AND METHODS OF USE

(71) Applicant: Boston Scientific Scimed, Inc., Maple Grove, MN (US)

(72) Inventor: Robert Frederick Bencini, Sannyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 938 days.

(21) Appl. No.: 16/370,394

(22) Filed: Mar. 29, 2019

(65) Prior Publication Data
US 2019/0223951 A1    Jul. 25, 2019

Related U.S. Application Data

(63) Continuation of application No. 14/613,155, filed on Feb. 3, 2015, now abandoned, which is a continuation
(Continued)

(51) Int. Cl.
*A61B 18/12* (2006.01)
*A61B 18/14* (2006.01)
(Continued)

(52) U.S. Cl.
CPC .............. *A61B 18/1492* (2013.01); *A61B 2017/00084* (2013.01); *A61B 2017/00526* (2013.01);
(Continued)

(58) Field of Classification Search
CPC ...... A61B 18/1492; A61B 2018/00214; A61B 2018/00577; A61B 2018/00791
See application file for complete search history.

(56) References Cited

U.S. PATENT DOCUMENTS 3,391,845 A    7/1968  Bessett
3,773,401 A    11/1973 Douklias
(Continued)

FOREIGN PATENT DOCUMENTS

AU    2014200766 B2    6/2015
CA       2682055 A1   10/2008
(Continued)

OTHER PUBLICATIONS

Extended European Search Report issued in EP Application 16182627.6, dated Nov. 8, 2016, 5 pages.
(Continued)

*Primary Examiner* — Daniel W Fowler
(74) *Attorney, Agent, or Firm* — Nelson Mullins Riley & Scarborough LLP

(57) ABSTRACT

Disclosed herein is a catheter device sized and shaped for vascular access that has an elongate body extending between a proximal end and a distal end. Further, the elongate body has at least one inner lumen configured to receive a fluid. The catheter also has an ablation electrode configured to provide ablative energy, wherein the electrode is located distally along the elongate body and includes a passageway fluidly connected to the lumen of the elongate body. Also, the catheter has a sensor configured to provide a signal representative of temperature, and an insulating chamber extending at least partially about the ablation electrode and configured to at least partially insulate the sensor.

14 Claims, 6 Drawing Sheets

Related U.S. Application Data of application No. 12/702,396, filed on Feb. 9, 2010, now Pat. No. 8,945,117.

(60) Provisional application No. 61/151,709, filed on Feb. 11, 2009.

(51) Int. Cl.
  *A61B 17/00* (2006.01)
  *A61B 18/00* (2006.01)

(52) U.S. Cl.
  CPC .............. *A61B 2018/00011* (2013.01); *A61B 2018/00101* (2013.01); *A61B 2018/00214* (2013.01); *A61B 2018/00577* (2013.01); *A61B 2018/00791* (2013.01); *Y10T 29/49002* (2015.01)

(56) References Cited

U.S. PATENT DOCUMENTS

| | | | |
|---|---|---|---|
| 4,466,443 | A | 8/1984 | Utsugi |
| 4,602,624 | A | 7/1986 | Naples et al. |
| 4,633,882 | A | 1/1987 | Matsuo et al. |
| 4,732,149 | A | 3/1988 | Sutter |
| 4,745,928 | A | 5/1988 | Webler et al. |
| 4,763,660 | A | 8/1988 | Kroll et al. |
| 4,945,912 | A | 8/1990 | Langberg |
| 4,966,145 | A | 10/1990 | Kikumoto et al. |
| 5,019,076 | A | 5/1991 | Yamanashi et al. |
| 5,029,588 | A | 7/1991 | Yock et al. |
| 5,114,423 | A | 5/1992 | Kasprzyk et al. |
| 5,151,100 | A | 9/1992 | Abele et al. |
| 5,178,150 | A | 1/1993 | Silverstein et al. |
| 5,217,460 | A | 6/1993 | Knoepfler |
| 5,230,349 | A | 7/1993 | Langberg |
| 5,238,004 | A | 8/1993 | Sahatjian et al. |
| 5,240,003 | A | 8/1993 | Lancee et al. |
| 5,242,441 | A | 9/1993 | Avitall |
| 5,254,088 | A | 10/1993 | Lundquist et al. |
| 5,277,201 | A | 1/1994 | Stern |
| 5,295,482 | A | 3/1994 | Clare et al. |
| 5,318,589 | A | 6/1994 | Lichtman |
| 5,324,284 | A | 6/1994 | Imran |
| 5,331,966 | A | 7/1994 | Bennett et al. |
| 5,334,193 | A | 8/1994 | Nardella |
| 5,341,807 | A | 8/1994 | Nardella |
| 5,377,685 | A | 1/1995 | Kazi et al. |
| 5,383,874 | A | 1/1995 | Jackson et al. |
| 5,385,146 | A | 1/1995 | Goldreyer |
| 5,385,148 | A | 1/1995 | Lesh et al. |
| 5,391,199 | A | 2/1995 | Ben-Haim |
| 5,398,683 | A | 3/1995 | Edwards et al. |
| 5,415,654 | A | 5/1995 | Daikuzono |
| 5,417,689 | A | 5/1995 | Fine |
| 5,423,811 | A | 6/1995 | Imran et al. |
| 5,447,529 | A | 9/1995 | Marchlinski et al. |
| 5,456,682 | A * | 10/1995 | Edwards ............ A61B 18/1206 600/549 |
| 5,462,521 | A | 10/1995 | Brucker et al. |
| 5,482,054 | A | 1/1996 | Slater et al. |
| 5,485,849 | A | 1/1996 | Panescu et al. |
| 5,494,042 | A | 2/1996 | Panescu et al. |
| 5,500,012 | A | 3/1996 | Brucker et al. |
| 5,520,683 | A | 5/1996 | Subramaniam et al. |
| 5,545,161 | A | 8/1996 | Imran |
| 5,571,088 | A | 11/1996 | Lennox et al. |
| 5,573,535 | A | 11/1996 | Viklund |
| 5,575,772 | A | 11/1996 | Lennox |
| 5,579,764 | A | 12/1996 | Goldreyer |
| 5,582,609 | A | 12/1996 | Swanson et al. |
| 5,643,197 | A | 7/1997 | Brucker et al. |
| 5,647,870 | A | 7/1997 | Kordis et al. |
| 5,676,693 | A | 10/1997 | LaFontaine |
| 5,688,267 | A * | 11/1997 | Panescu ................ A61N 1/403 606/41 |
| 5,718,701 | A | 2/1998 | Shai et al. |
| 5,722,402 | A | 3/1998 | Swanson et al. |
| 5,735,846 | A | 4/1998 | Panescu et al. |
| 5,762,067 | A | 6/1998 | Dunham et al. |
| 5,788,636 | A | 8/1998 | Curley |
| 5,792,064 | A | 8/1998 | Panescu et al. |
| 5,800,482 | A | 9/1998 | Pomeranz et al. |
| 5,810,802 | A * | 9/1998 | Panescu ............ A61B 18/1206 606/41 |
| 5,820,568 | A | 10/1998 | Willis |
| 5,830,213 | A | 11/1998 | Panescu et al. |
| 5,833,621 | A | 11/1998 | Panescu et al. |
| 5,836,875 | A | 11/1998 | Webster, Jr. |
| 5,836,990 | A | 11/1998 | Li |
| 5,868,735 | A | 2/1999 | Lafontaine |
| 5,871,483 | A | 2/1999 | Jackson et al. |
| 5,871,526 | A | 2/1999 | Gibbs et al. |
| 5,876,336 | A | 3/1999 | Swanson et al. |
| 5,885,278 | A | 3/1999 | Fleischman |
| 5,893,847 | A | 4/1999 | Kordis |
| 5,913,854 | A | 6/1999 | Maguire et al. |
| 5,913,856 | A | 6/1999 | Chia et al. |
| 5,916,213 | A | 6/1999 | Haissaguerre et al. |
| 5,919,188 | A | 7/1999 | Shearon et al. |
| 5,957,850 | A | 9/1999 | Marian et al. |
| 6,002,968 | A | 12/1999 | Edwards |
| 6,004,269 | A | 12/1999 | Crowley et al. |
| 6,006,755 | A | 12/1999 | Edwards |
| 6,027,500 | A | 2/2000 | Buckles et al. |
| 6,030,379 | A | 2/2000 | Panescu et al. |
| 6,042,559 | A * | 3/2000 | Dobak, III ............ A61M 1/369 604/113 |
| 6,050,267 | A | 4/2000 | Nardella et al. |
| 6,050,994 | A | 4/2000 | Sherman |
| 6,059,778 | A | 5/2000 | Sherman |
| 6,063,078 | A | 5/2000 | Wittkampf |
| 6,064,905 | A | 5/2000 | Webster et al. |
| 6,068,629 | A | 5/2000 | Haissaguerre et al. |
| 6,070,094 | A | 5/2000 | Swanson et al. |
| 6,071,281 | A | 6/2000 | Burnside et al. |
| 6,083,170 | A | 7/2000 | Ben-Haim |
| 6,083,222 | A | 7/2000 | Klein et al. |
| 6,099,524 | A | 8/2000 | Lipson et al. |
| 6,101,409 | A | 8/2000 | Swanson et al. |
| 6,116,027 | A | 9/2000 | Smith et al. |
| 6,120,476 | A | 9/2000 | Fung et al. |
| 6,162,184 | A | 12/2000 | Swanson et al. |
| 6,165,123 | A | 12/2000 | Thompson |
| 6,171,275 | B1 | 1/2001 | Webster, Jr. |
| 6,171,305 | B1 | 1/2001 | Sherman |
| 6,200,314 | B1 | 3/2001 | Sherman |
| 6,206,831 | B1 | 3/2001 | Suorsa et al. |
| 6,210,337 | B1 | 4/2001 | Dunham et al. |
| 6,216,027 | B1 | 4/2001 | Willis et al. |
| 6,224,557 | B1 | 5/2001 | Ziel et al. |
| 6,233,491 | B1 | 5/2001 | Kordis et al. |
| 6,241,724 | B1 | 6/2001 | Fleischman et al. |
| 6,241,754 | B1 | 6/2001 | Swanson et al. |
| 6,258,087 | B1 | 7/2001 | Edwards et al. |
| 6,270,493 | B1 | 8/2001 | Lalonde et al. |
| 6,290,697 | B1 | 9/2001 | Tu et al. |
| 6,352,534 | B1 | 3/2002 | Paddock et al. |
| 6,395,325 | B1 | 5/2002 | Hedge et al. |
| 6,400,981 | B1 | 6/2002 | Govari |
| 6,423,002 | B1 | 7/2002 | Hossack |
| 6,475,213 | B1 | 11/2002 | Swanson et al. |
| 6,488,678 | B2 | 12/2002 | Sherman |
| 6,491,710 | B2 | 12/2002 | Satake |
| 6,500,174 | B1 | 12/2002 | Maguire et al. |
| 6,508,767 | B2 | 1/2003 | Burns et al. |
| 6,508,769 | B2 | 1/2003 | Bonnefous |
| 6,508,803 | B1 | 1/2003 | Horikawa et al. |
| 6,514,249 | B1 | 2/2003 | Maguire et al. |
| 6,516,667 | B1 | 2/2003 | Broad et al. |
| 6,517,533 | B1 | 2/2003 | Swaminathan |
| 6,517,534 | B1 | 2/2003 | McGovern et al. |
| 6,537,271 | B1 | 3/2003 | Murray et al. |
| 6,544,175 | B1 | 4/2003 | Newman |
| 6,546,270 | B1 | 4/2003 | Goldin et al. |

(56) References Cited

U.S. PATENT DOCUMENTS

| | | |
|---|---|---|
| 6,547,788 B1 | 4/2003 | Maguire et al. |
| 6,569,160 B1 | 5/2003 | Goldin et al. |
| 6,569,162 B2 | 5/2003 | He |
| 6,572,547 B2 | 6/2003 | Miller et al. |
| 6,575,966 B2 | 6/2003 | Lane et al. |
| 6,575,969 B1 | 6/2003 | Rittman et al. |
| 6,579,278 B1 | 6/2003 | Bencini |
| 6,582,372 B2 | 6/2003 | Poland |
| 6,584,345 B2 | 6/2003 | Govari |
| 6,589,182 B1 | 7/2003 | Loftman et al. |
| 6,589,238 B2 | 7/2003 | Edwards et al. |
| 6,592,525 B2 | 7/2003 | Miller et al. |
| 6,602,242 B1 | 8/2003 | Fung et al. |
| 6,620,103 B1 | 9/2003 | Bruce et al. |
| 6,632,179 B2 | 10/2003 | Wilson et al. |
| 6,638,222 B2 | 10/2003 | Chandrasekaran et al. |
| 6,640,120 B1 | 10/2003 | Swanson et al. |
| 6,647,281 B2 | 11/2003 | Morency |
| 6,656,174 B1 | 12/2003 | Hegde et al. |
| 6,658,279 B2 | 12/2003 | Swanson et al. |
| 6,663,573 B2 | 12/2003 | Goldin |
| 6,663,622 B1 | 12/2003 | Foley et al. |
| 6,666,862 B2 | 12/2003 | Jain et al. |
| 6,673,067 B1 | 1/2004 | Peyman |
| 6,676,606 B2 | 1/2004 | Simpson et al. |
| 6,692,441 B1 | 2/2004 | Poland et al. |
| 6,705,992 B2 | 3/2004 | Gatzke |
| 6,709,396 B2 | 3/2004 | Flesch et al. |
| 6,711,429 B1 | 3/2004 | Gilboa et al. |
| 6,719,756 B1 | 4/2004 | Muntermann |
| 6,723,094 B1 | 4/2004 | Desinger |
| 6,735,465 B2 | 5/2004 | Panescu |
| 6,736,814 B2 | 5/2004 | Manna et al. |
| 6,743,174 B2 | 6/2004 | Ng et al. |
| 6,773,402 B2 | 8/2004 | Govari et al. |
| 6,776,758 B2 | 8/2004 | Peszynski et al. |
| 6,796,979 B2 | 9/2004 | Lentz |
| 6,796,980 B2 | 9/2004 | Hall |
| 6,804,545 B2 | 10/2004 | Fuimaono et al. |
| 6,811,550 B2 | 11/2004 | Holland et al. |
| 6,824,517 B2 | 11/2004 | Salgo et al. |
| 6,837,884 B2 | 1/2005 | Woloszko |
| 6,845,257 B2 | 1/2005 | Fuimaono et al. |
| 6,845,264 B1 | 1/2005 | Skladnev et al. |
| 6,917,834 B2 | 7/2005 | Koblish et al. |
| 6,922,579 B2 | 7/2005 | Taimisto et al. |
| 6,923,808 B2 | 8/2005 | Taimisto |
| 6,932,811 B2 | 8/2005 | Hooven et al. |
| 6,945,938 B2 | 9/2005 | Grunwald |
| 6,950,689 B1 | 9/2005 | Willis et al. |
| 6,952,615 B2 | 10/2005 | Satake |
| 6,958,040 B2 | 10/2005 | Oliver et al. |
| 6,972,016 B2 | 12/2005 | Hill et al. |
| 7,001,383 B2 | 2/2006 | Keidar |
| 7,037,264 B2 | 5/2006 | Poland |
| 7,047,068 B2 | 5/2006 | Haissaguerre |
| 7,097,643 B2 | 8/2006 | Cornelius et al. |
| 7,099,711 B2 | 8/2006 | Fuimaono et al. |
| 7,105,122 B2 | 9/2006 | Karason |
| 7,112,198 B2 | 9/2006 | Satake |
| 7,115,122 B1 | 10/2006 | Swanson et al. |
| 7,123,951 B2 | 10/2006 | Fuimaono et al. |
| 7,125,409 B2 | 10/2006 | Truckai et al. |
| 7,131,947 B2 | 11/2006 | Demers |
| 7,166,075 B2 | 1/2007 | Varghese et al. |
| 7,181,262 B2 | 2/2007 | Fuimaono et al. |
| 7,198,625 B1 * | 4/2007 | Hui .................. A61B 18/1482 606/41 |
| 7,220,233 B2 | 5/2007 | Nita et al. |
| 7,232,433 B1 | 6/2007 | Schlesinger et al. |
| 7,247,155 B2 | 7/2007 | Hoey et al. |
| 7,270,634 B2 | 9/2007 | Scampini et al. |
| 7,288,088 B2 | 10/2007 | Swanson |
| 7,291,142 B2 | 11/2007 | Eberl et al. |
| 7,306,561 B2 | 12/2007 | Sathyanarayana |
| 7,335,052 B2 | 2/2008 | D Sa |
| 7,347,820 B2 | 3/2008 | Bonnefous |
| 7,347,821 B2 | 3/2008 | Skyba et al. |
| 7,347,857 B2 | 3/2008 | Anderson et al. |
| 7,361,144 B2 | 4/2008 | Levrier et al. |
| 7,422,591 B2 | 9/2008 | Phan |
| 7,438,714 B2 | 10/2008 | Phan |
| 7,455,669 B2 | 11/2008 | Swanson |
| 7,488,289 B2 | 2/2009 | Suorsa et al. |
| 7,507,205 B2 | 3/2009 | Borovsky et al. |
| 7,507,237 B2 | 3/2009 | Geistert |
| 7,519,410 B2 | 4/2009 | Taimisto et al. |
| 7,529,393 B2 | 5/2009 | Peszynski et al. |
| 7,534,207 B2 | 5/2009 | Shehada et al. |
| 7,544,164 B2 | 6/2009 | Knowles et al. |
| 7,549,988 B2 | 6/2009 | Eberl et al. |
| 7,569,052 B2 | 8/2009 | Phan et al. |
| 7,578,791 B2 | 8/2009 | Rafter |
| 7,582,083 B2 | 9/2009 | Swanson |
| 7,585,310 B2 | 9/2009 | Phan et al. |
| 7,610,073 B2 | 10/2009 | Fuimaono et al. |
| 7,648,462 B2 | 1/2010 | Jenkins et al. |
| 7,697,972 B2 | 4/2010 | Verard et al. |
| 7,704,208 B2 | 4/2010 | Thiele |
| 7,720,420 B2 | 5/2010 | Kajita |
| 7,727,231 B2 | 6/2010 | Swanson |
| 7,736,362 B2 | 6/2010 | Eberl et al. |
| 7,740,629 B2 | 6/2010 | Anderson et al. |
| 7,758,508 B1 | 7/2010 | Thiele et al. |
| 7,766,833 B2 | 8/2010 | Lee et al. |
| 7,776,033 B2 | 8/2010 | Swanson |
| 7,785,324 B2 | 8/2010 | Eberl |
| 7,794,398 B2 | 9/2010 | Salgo |
| 7,796,789 B2 | 9/2010 | Salgo et al. |
| 7,799,025 B2 | 9/2010 | Wellman |
| 7,815,572 B2 | 10/2010 | Loupas |
| 7,819,863 B2 | 10/2010 | Eggers et al. |
| 7,837,624 B1 | 11/2010 | Hossack et al. |
| 7,859,170 B2 | 12/2010 | Knowles et al. |
| 7,862,561 B2 | 1/2011 | Swanson et al. |
| 7,862,562 B2 | 1/2011 | Eberl |
| 7,879,029 B2 | 2/2011 | Jimenez |
| 7,892,228 B2 | 2/2011 | Landis et al. |
| 7,894,871 B2 | 2/2011 | Wittkampf et al. |
| 7,918,850 B2 | 4/2011 | Govari et al. |
| 7,957,817 B1 | 6/2011 | Gillespie et al. |
| 7,996,085 B2 | 8/2011 | Levin |
| 8,016,822 B2 | 9/2011 | Swanson |
| 8,048,028 B2 | 11/2011 | Horn et al. |
| 8,103,327 B2 | 1/2012 | Harlev et al. |
| 8,128,617 B2 | 3/2012 | Bencini et al. |
| 8,160,690 B2 | 4/2012 | Wilfley et al. |
| 8,162,935 B2 | 4/2012 | Paul et al. |
| 8,183,441 B2 | 5/2012 | Cukadar |
| 8,265,745 B2 | 9/2012 | Hauck et al. |
| 8,267,926 B2 | 9/2012 | Paul et al. |
| 8,290,578 B2 | 10/2012 | Schneider |
| 8,317,783 B2 | 11/2012 | Cao et al. |
| 8,369,922 B2 | 2/2013 | Paul et al. |
| 8,400,164 B2 | 3/2013 | Osadchy et al. |
| 8,403,925 B2 | 3/2013 | Miller et al. |
| 8,406,866 B2 | 3/2013 | Deno et al. |
| 8,414,579 B2 | 4/2013 | Kim et al. |
| 8,449,535 B2 | 5/2013 | Deno et al. |
| 8,454,538 B2 | 6/2013 | Wittkampf et al. |
| 8,454,589 B2 | 6/2013 | Deno et al. |
| 8,489,184 B2 | 7/2013 | Wilfley et al. |
| 8,579,889 B2 | 11/2013 | Bencini |
| 8,583,215 B2 | 11/2013 | Lichtenstein |
| 8,603,084 B2 | 12/2013 | Fish et al. |
| 8,603,085 B2 | 12/2013 | Jimenez |
| 8,644,950 B2 | 2/2014 | Hauck |
| 8,657,814 B2 | 2/2014 | Werneth et al. |
| 8,672,936 B2 | 3/2014 | Thao |
| 8,679,109 B2 | 3/2014 | Paul et al. |
| 8,728,077 B2 | 5/2014 | Paul et al. |
| 8,740,900 B2 | 6/2014 | Kim et al. |
| 8,755,860 B2 | 6/2014 | Paul et al. |
| 8,771,343 B2 | 7/2014 | Weber et al. |

(56) References Cited

U.S. PATENT DOCUMENTS

| | | |
|---|---|---|
| 8,876,817 B2 | 11/2014 | Avitall et al. |
| 8,894,643 B2 | 11/2014 | Watson et al. |
| 8,906,011 B2 | 12/2014 | Gelbart et al. |
| 8,945,015 B2 | 2/2015 | Rankin et al. |
| 8,945,117 B2 | 2/2015 | Bencini |
| 8,998,890 B2 | 4/2015 | Paul et al. |
| 9,044,300 B2 | 6/2015 | Belhe et al. |
| 9,089,340 B2 | 7/2015 | Hastings et al. |
| 9,125,565 B2 | 9/2015 | Hauck |
| 9,125,668 B2 | 9/2015 | Subramaniam et al. |
| 9,168,004 B2 | 10/2015 | Gliner et al. |
| 9,173,586 B2 | 11/2015 | Deno et al. |
| 9,211,156 B2 | 12/2015 | Kim et al. |
| 9,241,687 B2 | 1/2016 | McGee |
| 9,241,761 B2 | 1/2016 | Rankin et al. |
| 9,254,163 B2 | 2/2016 | Paul et al. |
| 9,265,434 B2 | 2/2016 | Merschon et al. |
| 9,271,782 B2 | 3/2016 | Paul et al. |
| 9,283,026 B2 | 3/2016 | Paul et al. |
| 9,370,329 B2 | 6/2016 | Tun et al. |
| 9,393,072 B2 | 7/2016 | Kim et al. |
| 9,463,064 B2 | 10/2016 | Subramaniam et al. |
| 9,603,659 B2 | 3/2017 | Subramaniam et al. |
| 9,622,897 B1 | 4/2017 | Stangenes et al. |
| 9,743,854 B2 | 8/2017 | Stewart et al. |
| 9,757,191 B2 | 9/2017 | Avitall et al. |
| 9,956,035 B2 | 5/2018 | Govari et al. |
| 10,524,684 B2 | 1/2020 | Fay et al. |
| 2001/0008967 A1 | 7/2001 | Sherman |
| 2001/0029371 A1 | 10/2001 | Kordis |
| 2001/0031921 A1 | 10/2001 | Bonnefous |
| 2001/0034518 A1 | 10/2001 | Edwards et al. |
| 2001/0039381 A1 | 11/2001 | Burns et al. |
| 2002/0007180 A1 | 1/2002 | Wittenberger et al. |
| 2002/0045893 A1 | 4/2002 | Lane et al. |
| 2002/0065512 A1 | 5/2002 | Fjield et al. |
| 2002/0072663 A1 | 6/2002 | Fuimaono et al. |
| 2002/0082503 A1 | 6/2002 | Chandrasekaran et al. |
| 2002/0087208 A1 | 7/2002 | Koblish et al. |
| 2002/0091384 A1 | 7/2002 | Hooven et al. |
| 2002/0107447 A1 | 8/2002 | Suorsa et al. |
| 2002/0111548 A1 | 8/2002 | Swanson et al. |
| 2002/0147391 A1 | 10/2002 | Morency |
| 2002/0151807 A1 | 10/2002 | Goldin |
| 2002/0161306 A1 | 10/2002 | Govari |
| 2002/0165448 A1 | 11/2002 | Ben-Haim et al. |
| 2002/0169445 A1 | 11/2002 | Jain et al. |
| 2002/0183731 A1 | 12/2002 | Holland et al. |
| 2002/0183735 A1 | 12/2002 | Edwards et al. |
| 2002/0198521 A1 | 12/2002 | Maguire |
| 2003/0004505 A1 | 1/2003 | Bencini et al. |
| 2003/0004506 A1 | 1/2003 | Messing |
| 2003/0013955 A1 | 1/2003 | Poland |
| 2003/0013958 A1 | 1/2003 | Govari et al. |
| 2003/0014051 A1 | 1/2003 | Woloszko |
| 2003/0014095 A1 | 1/2003 | Kramer et al. |
| 2003/0028103 A1 | 2/2003 | Miller et al. |
| 2003/0028104 A1 | 2/2003 | Wilson et al. |
| 2003/0065371 A1 | 4/2003 | Satake |
| 2003/0078509 A1 | 4/2003 | Panescu |
| 2003/0088240 A1 | 5/2003 | Saadat |
| 2003/0092993 A1 | 5/2003 | Grunwald |
| 2003/0097125 A1 | 5/2003 | Hall |
| 2003/0158548 A1 | 8/2003 | Phan et al. |
| 2003/0158549 A1 | 8/2003 | Swanson |
| 2003/0163045 A1 | 8/2003 | Gatzke |
| 2003/0163130 A1 | 8/2003 | Manna et al. |
| 2003/0171672 A1 | 9/2003 | Varghese et al. |
| 2003/0187353 A1 | 10/2003 | Ng et al. |
| 2003/0191380 A1 | 10/2003 | Fuimaono et al. |
| 2003/0195407 A1 | 10/2003 | Fuimaono et al. |
| 2003/0208124 A1 | 11/2003 | Poland |
| 2003/0229285 A1 | 12/2003 | Simpson et al. |
| 2003/0229286 A1 | 12/2003 | Lenker |
| 2003/0236462 A1 | 12/2003 | Salgo et al. |
| 2004/0006268 A1 | 1/2004 | Gilboa et al. |
| 2004/0010200 A1 | 1/2004 | Sweeney |
| 2004/0015084 A1 | 1/2004 | Flesch et al. |
| 2004/0073114 A1 | 4/2004 | Oliver et al. |
| 2004/0073118 A1 | 4/2004 | Peszynski et al. |
| 2004/0078036 A1 | 4/2004 | Keidar |
| 2004/0082860 A1 | 4/2004 | Haissaguerre |
| 2004/0092806 A1 | 5/2004 | Sagon et al. |
| 2004/0097805 A1 | 5/2004 | Verard et al. |
| 2004/0116793 A1 | 6/2004 | Taimisto et al. |
| 2004/0116916 A1 | 6/2004 | Lentz |
| 2004/0137098 A1 | 7/2004 | Karason |
| 2004/0147920 A1 | 7/2004 | Keidar |
| 2004/0158139 A1 | 8/2004 | Fuimaono et al. |
| 2004/0158140 A1 | 8/2004 | Fuimaono et al. |
| 2004/0158238 A1 | 8/2004 | Lalonde et al. |
| 2004/0158270 A1 | 8/2004 | Wyzgala et al. |
| 2004/0162556 A1 | 8/2004 | Swanson |
| 2004/0167509 A1 | 8/2004 | Taimisto |
| 2004/0172110 A1 | 9/2004 | Satake |
| 2004/0186467 A1 | 9/2004 | Swanson et al. |
| 2004/0193042 A1 | 9/2004 | Scampini et al. |
| 2004/0204670 A1 | 10/2004 | Nita et al. |
| 2004/0210136 A1 | 10/2004 | Varghese et al. |
| 2004/0215177 A1 | 10/2004 | Swanson |
| 2004/0215183 A1 | 10/2004 | Hoey et al. |
| 2004/0215186 A1 | 10/2004 | Cornelius et al. |
| 2004/0225219 A1 | 11/2004 | Demers |
| 2004/0236192 A1 | 11/2004 | Necola et al. |
| 2004/0267125 A1 | 12/2004 | Skyba et al. |
| 2005/0033331 A1 | 2/2005 | Burnett et al. |
| 2005/0059862 A1 | 3/2005 | Phan |
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2005/0065508 A1 | 3/2005 | Johnson et al. |
| 2005/0070894 A1 | 3/2005 | McClurken |
| 2005/0090817 A1 | 4/2005 | Phan |
| 2005/0119545 A1 | 6/2005 | Swanson |
| 2005/0119648 A1 | 6/2005 | Swanson |
| 2005/0119649 A1 | 6/2005 | Swanson |
| 2005/0119653 A1 | 6/2005 | Swanson |
| 2005/0119654 A1 | 6/2005 | Swanson et al. |
| 2005/0124881 A1 | 6/2005 | Kanai et al. |
| 2005/0124899 A1 | 6/2005 | Byrd et al. |
| 2005/0165391 A1 | 7/2005 | Maguire et al. |
| 2005/0187544 A1 | 8/2005 | Swanson et al. |
| 2005/0203505 A1 | 9/2005 | Megerman et al. |
| 2005/0203597 A1 | 9/2005 | Yamazaki et al. |
| 2005/0215993 A1 | 9/2005 | Phan |
| 2005/0228286 A1 | 10/2005 | Messerly |
| 2005/0228290 A1 | 10/2005 | Borovsky et al. |
| 2005/0228504 A1 | 10/2005 | Demarais |
| 2005/0251121 A1 | 11/2005 | Swanson |
| 2005/0251122 A1 | 11/2005 | Swanson |
| 2005/0251123 A1 | 11/2005 | Eberl et al. |
| 2005/0273060 A1 | 12/2005 | Levy et al. |
| 2005/0288667 A1 | 12/2005 | Thompson et al. |
| 2006/0030919 A1 | 2/2006 | Mrva et al. |
| 2006/0047277 A1 | 3/2006 | Eberl et al. |
| 2006/0052698 A1 | 3/2006 | Loupas |
| 2006/0058657 A1 | 3/2006 | Sathyanarayana |
| 2006/0058668 A1 | 3/2006 | Levrier et al. |
| 2006/0074309 A1 | 4/2006 | Bonnefous |
| 2006/0089634 A1 | 4/2006 | Anderson et al. |
| 2006/0100522 A1 | 5/2006 | Yuan et al. |
| 2006/0155272 A1 | 7/2006 | Swanson |
| 2006/0155273 A1 | 7/2006 | Swanson |
| 2006/0155274 A1 | 7/2006 | Swanson et al. |
| 2006/0161146 A1 | 7/2006 | Cornelius et al. |
| 2006/0161201 A1 | 7/2006 | Phan et al. |
| 2006/0182320 A1 | 8/2006 | Peszynski et al. |
| 2006/0184112 A1 | 8/2006 | Horn et al. |
| 2006/0193504 A1 | 8/2006 | Salgo et al. |
| 2006/0195079 A1 | 8/2006 | Eberl |
| 2006/0195080 A1 | 8/2006 | Ebert |
| 2006/0195081 A1 | 8/2006 | Landis et al. |
| 2006/0206109 A1 | 9/2006 | Swanson |

(56) References Cited

U.S. PATENT DOCUMENTS

| | | |
|---|---|---|
| 2006/0224153 A1 | 10/2006 | Fischell et al. |
| 2006/0247607 A1 | 11/2006 | Cornelius et al. |
| 2006/0247683 A1 | 11/2006 | Danek |
| 2006/0253028 A1 | 11/2006 | Lam et al. |
| 2006/0253116 A1 | 11/2006 | Avitall et al. |
| 2006/0258940 A1 | 11/2006 | D Sa |
| 2006/0271032 A1 | 11/2006 | Chin et al. |
| 2006/0271034 A1 | 11/2006 | Swanson |
| 2007/0003811 A1 | 1/2007 | Zerfass et al. |
| 2007/0016019 A1 | 1/2007 | Salgo |
| 2007/0016054 A1 | 1/2007 | Cao et al. |
| 2007/0016059 A1 | 1/2007 | Morimoto et al. |
| 2007/0016228 A1 | 1/2007 | Salas |
| 2007/0021744 A1 | 1/2007 | Creighton |
| 2007/0032724 A1 | 2/2007 | Thiele |
| 2007/0049925 A1 | 3/2007 | Phan et al. |
| 2007/0055225 A1 | 3/2007 | Dodd et al. |
| 2007/0073135 A1 | 3/2007 | Lee et al. |
| 2007/0083193 A1 | 4/2007 | Werneth et al. |
| 2007/0088345 A1 | 4/2007 | Larson et al. |
| 2007/0123764 A1 | 5/2007 | Thao |
| 2007/0129633 A1 | 6/2007 | Lee et al. |
| 2007/0135700 A1 | 6/2007 | Taimisto et al. |
| 2007/0156128 A1 | 7/2007 | Jimenez |
| 2007/0165916 A1 | 7/2007 | Cloutier et al. |
| 2007/0167813 A1 | 7/2007 | Lee et al. |
| 2007/0179375 A1 | 8/2007 | Fuimaono et al. |
| 2007/0181139 A1 | 8/2007 | Hauck |
| 2007/0198007 A1 | 8/2007 | Govari et al. |
| 2007/0225610 A1 | 9/2007 | Mickley et al. |
| 2007/0238997 A1 | 10/2007 | Camus |
| 2007/0239017 A1 | 10/2007 | Knowles et al. |
| 2007/0270791 A1 | 11/2007 | Wang et al. |
| 2007/0270794 A1 | 11/2007 | Anderson et al. |
| 2007/0276239 A1 | 11/2007 | Rafter |
| 2008/0004691 A1 | 1/2008 | Weber et al. |
| 2008/0009733 A1 | 1/2008 | Saksena |
| 2008/0015568 A1 | 1/2008 | Paul et al. |
| 2008/0025145 A1 | 1/2008 | Peszynski et al. |
| 2008/0051841 A1 | 2/2008 | Swerdlow et al. |
| 2008/0056750 A1 | 3/2008 | Kajita |
| 2008/0058836 A1 | 3/2008 | Moll et al. |
| 2008/0086073 A1 | 4/2008 | McDaniel |
| 2008/0091109 A1 | 4/2008 | Abraham |
| 2008/0140065 A1 | 6/2008 | Rioux et al. |
| 2008/0147060 A1* | 6/2008 | Choi .............. A61B 18/1477 606/42 |
| 2008/0161668 A1 | 7/2008 | Wittkampf et al. |
| 2008/0161705 A1 | 7/2008 | Podmore et al. |
| 2008/0161795 A1 | 7/2008 | Wang et al. |
| 2008/0161796 A1 | 7/2008 | Cao et al. |
| 2008/0195089 A1 | 8/2008 | Thiagalingam et al. |
| 2008/0228111 A1 | 9/2008 | Nita |
| 2008/0243214 A1 | 10/2008 | Koblish |
| 2008/0249518 A1 | 10/2008 | Warnking et al. |
| 2008/0255470 A1 | 10/2008 | Hauck et al. |
| 2008/0275428 A1 | 11/2008 | Tegg et al. |
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0281322 A1 | 11/2008 | Sherman et al. |
| 2008/0287803 A1 | 11/2008 | Li et al. |
| 2008/0288038 A1 | 11/2008 | Paul et al. |
| 2008/0300454 A1 | 12/2008 | Goto |
| 2008/0300589 A1 | 12/2008 | Paul et al. |
| 2008/0312521 A1 | 12/2008 | Solomon |
| 2008/0312713 A1 | 12/2008 | Wilfley et al. |
| 2009/0000383 A1 | 1/2009 | Knowles et al. |
| 2009/0005771 A1 | 1/2009 | Lieber et al. |
| 2009/0024119 A1 | 1/2009 | Wellman |
| 2009/0030312 A1 | 1/2009 | Hadjicostis |
| 2009/0048591 A1 | 2/2009 | Ibrahim et al. |
| 2009/0056344 A1 | 3/2009 | Poch |
| 2009/0062790 A1 | 3/2009 | Malchano et al. |
| 2009/0062795 A1 | 3/2009 | Vakharia et al. |
| 2009/0069807 A1 | 3/2009 | Eggers et al. |
| 2009/0076390 A1 | 3/2009 | Lee et al. |
| 2009/0088631 A1 | 4/2009 | Dietz et al. |
| 2009/0093810 A1 | 4/2009 | Subramaniam et al. |
| 2009/0093811 A1 | 4/2009 | Koblish et al. |
| 2009/0099472 A1 | 4/2009 | Remmert et al. |
| 2009/0131930 A1 | 5/2009 | Gelbart et al. |
| 2009/0131932 A1 | 5/2009 | Vakharia et al. |
| 2009/0163904 A1 | 6/2009 | Miller et al. |
| 2009/0171235 A1 | 7/2009 | Schneider et al. |
| 2009/0171274 A1 | 7/2009 | Harlev et al. |
| 2009/0171341 A1 | 7/2009 | Pope et al. |
| 2009/0171345 A1 | 7/2009 | Miller et al. |
| 2009/0177069 A1 | 7/2009 | Razavi |
| 2009/0177111 A1 | 7/2009 | Miller et al. |
| 2009/0182316 A1 | 7/2009 | Bencini |
| 2009/0209950 A1 | 8/2009 | Starksen |
| 2009/0216125 A1 | 8/2009 | Lenker |
| 2009/0240247 A1 | 9/2009 | Rioux et al. |
| 2009/0259274 A1 | 10/2009 | Simon et al. |
| 2009/0275827 A1 | 11/2009 | Aiken et al. |
| 2009/0281541 A1 | 11/2009 | Ibrahim et al. |
| 2009/0287202 A1 | 11/2009 | Ingle et al. |
| 2009/0292209 A1 | 11/2009 | Hadjicostis |
| 2009/0299355 A1 | 12/2009 | Bencini et al. |
| 2009/0299360 A1 | 12/2009 | Ormsby |
| 2009/0306643 A1 | 12/2009 | Pappone et al. |
| 2010/0010487 A1 | 1/2010 | Phan et al. |
| 2010/0030204 A1 | 2/2010 | Stein et al. |
| 2010/0057072 A1 | 3/2010 | Roman et al. |
| 2010/0069921 A1 | 3/2010 | Miller et al. |
| 2010/0076402 A1 | 3/2010 | Mazzone et al. |
| 2010/0076426 A1 | 3/2010 | De et al. |
| 2010/0094274 A1 | 4/2010 | Narayan et al. |
| 2010/0106155 A1 | 4/2010 | Anderson et al. |
| 2010/0113938 A1 | 5/2010 | Park et al. |
| 2010/0114092 A1 | 5/2010 | Eisele et al. |
| 2010/0117659 A1 | 5/2010 | Osadchy et al. |
| 2010/0121393 A1 | 5/2010 | Levin |
| 2010/0137944 A1 | 6/2010 | Zhu |
| 2010/0145221 A1 | 6/2010 | Brunnett et al. |
| 2010/0152728 A1 | 6/2010 | Park et al. |
| 2010/0168557 A1 | 7/2010 | Deno et al. |
| 2010/0168568 A1 | 7/2010 | Sliwa |
| 2010/0168570 A1 | 7/2010 | Sliwa et al. |
| 2010/0168735 A1 | 7/2010 | Deno et al. |
| 2010/0168831 A1 | 7/2010 | Korivi et al. |
| 2010/0228247 A1 | 9/2010 | Paul et al. |
| 2010/0241117 A1 | 9/2010 | Paul et al. |
| 2010/0249599 A1 | 9/2010 | Hastings et al. |
| 2010/0249603 A1 | 9/2010 | Hastings et al. |
| 2010/0249604 A1 | 9/2010 | Hastings et al. |
| 2010/0262140 A1 | 10/2010 | Watson et al. |
| 2010/0268217 A1 | 10/2010 | Habib |
| 2010/0286690 A1 | 11/2010 | Paul et al. |
| 2010/0298823 A1 | 11/2010 | Cao et al. |
| 2010/0298826 A1 | 11/2010 | Leo et al. |
| 2010/0331658 A1 | 12/2010 | Kim et al. |
| 2011/0028820 A1 | 2/2011 | Lau et al. |
| 2011/0034915 A1 | 2/2011 | Ibrahim et al. |
| 2011/0071400 A1 | 3/2011 | Hastings et al. |
| 2011/0071401 A1 | 3/2011 | Hastings et al. |
| 2011/0106075 A1 | 5/2011 | Jimenez |
| 2011/0112569 A1 | 5/2011 | Friedman et al. |
| 2011/0118727 A1 | 5/2011 | Fish et al. |
| 2011/0125008 A1 | 5/2011 | Wittkampf et al. |
| 2011/0125143 A1 | 5/2011 | Gross et al. |
| 2011/0125150 A1 | 5/2011 | Deno et al. |
| 2011/0130648 A1 | 6/2011 | Beeckler et al. |
| 2011/0137151 A1 | 6/2011 | Lichtenstein |
| 2011/0137153 A1 | 6/2011 | Govari et al. |
| 2011/0144491 A1 | 6/2011 | Sliwa et al. |
| 2011/0144524 A1 | 6/2011 | Fish et al. |
| 2011/0160584 A1 | 6/2011 | Paul et al. |
| 2011/0237933 A1 | 9/2011 | Cohen |
| 2011/0282249 A1 | 11/2011 | Tsoref et al. |
| 2011/0319782 A1 | 12/2011 | Sweeney et al. |
| 2012/0004547 A1 | 1/2012 | Harks et al. |
| 2012/0004621 A1 | 1/2012 | Shaw et al. |

(56) References Cited

U.S. PATENT DOCUMENTS

| | | |
|---|---|---|
| 2012/0029504 A1 | 2/2012 | Afonso et al. |
| 2012/0071870 A1 | 3/2012 | Salahieh et al. |
| 2012/0095347 A1 | 4/2012 | Adam et al. |
| 2012/0101398 A1 | 4/2012 | Ramanathan et al. |
| 2012/0116537 A1 | 5/2012 | Liebetanz |
| 2012/0136346 A1 | 5/2012 | Condie et al. |
| 2012/0136348 A1 | 5/2012 | Condie et al. |
| 2012/0136351 A1 | 5/2012 | Weekamp et al. |
| 2012/0165702 A1 | 6/2012 | Hauck |
| 2012/0172698 A1 | 7/2012 | Teo et al. |
| 2012/0172727 A1 | 7/2012 | Hastings et al. |
| 2012/0172871 A1 | 7/2012 | Hastings et al. |
| 2012/0232460 A1 | 9/2012 | Raven et al. |
| 2012/0238897 A1 | 9/2012 | Wilfley et al. |
| 2012/0310064 A1 | 12/2012 | McGee |
| 2012/0323237 A1 | 12/2012 | Paul et al. |
| 2012/0330304 A1 | 12/2012 | Vegesna et al. |
| 2013/0023784 A1 | 1/2013 | Schneider et al. |
| 2013/0023897 A1 | 1/2013 | Wallace |
| 2013/0060245 A1 | 3/2013 | Grunewald et al. |
| 2013/0066312 A1 | 3/2013 | Subramaniam et al. |
| 2013/0066315 A1 | 3/2013 | Subramaniam et al. |
| 2013/0079763 A1 | 3/2013 | Heckel et al. |
| 2013/0085416 A1 | 4/2013 | Mest |
| 2013/0138099 A1 | 5/2013 | Paul et al. |
| 2013/0165926 A1 | 6/2013 | Mathur et al. |
| 2013/0172715 A1 | 7/2013 | Just et al. |
| 2013/0172742 A1 | 7/2013 | Rankin et al. |
| 2013/0172875 A1 | 7/2013 | Govari et al. |
| 2013/0184706 A1 | 7/2013 | Gelbart et al. |
| 2013/0190747 A1 | 7/2013 | Koblish et al. |
| 2013/0197363 A1 | 8/2013 | Rankin et al. |
| 2013/0197507 A1 | 8/2013 | Kim et al. |
| 2013/0226169 A1 | 8/2013 | Miller et al. |
| 2013/0274582 A1 | 10/2013 | Afonso et al. |
| 2013/0331739 A1 | 12/2013 | Gertner |
| 2013/0345537 A1 | 12/2013 | Thakur et al. |
| 2014/0012251 A1 | 1/2014 | Himmelstein et al. |
| 2014/0051959 A1 | 2/2014 | Gliner et al. |
| 2014/0058375 A1 | 2/2014 | Koblish |
| 2014/0066764 A1 | 3/2014 | Subramaniam et al. |
| 2014/0073893 A1 | 3/2014 | Bencini |
| 2014/0075753 A1 | 3/2014 | Haarer et al. |
| 2014/0081111 A1 | 3/2014 | Tun et al. |
| 2014/0081112 A1 | 3/2014 | Kim et al. |
| 2014/0081113 A1 | 3/2014 | Cohen et al. |
| 2014/0081262 A1 | 3/2014 | Koblish et al. |
| 2014/0100563 A1 | 4/2014 | Govari et al. |
| 2014/0107430 A1 | 4/2014 | Deno et al. |
| 2014/0107453 A1 | 4/2014 | Maskara et al. |
| 2014/0107636 A1 | 4/2014 | Bencini |
| 2014/0121660 A1 | 5/2014 | Hauck |
| 2014/0128757 A1 | 5/2014 | Banet et al. |
| 2014/0142393 A1 | 5/2014 | Piskun et al. |
| 2014/0194867 A1 | 7/2014 | Fish et al. |
| 2014/0200429 A1 | 7/2014 | Spector et al. |
| 2014/0200430 A1 | 7/2014 | Spector |
| 2014/0214028 A1 | 7/2014 | Gelbart et al. |
| 2014/0228713 A1 | 8/2014 | Thao et al. |
| 2014/0243917 A1 | 8/2014 | Morley et al. |
| 2014/0261985 A1 | 9/2014 | Selkee |
| 2014/0275916 A1 | 9/2014 | Nabutovsky et al. |
| 2014/0276052 A1 | 9/2014 | Rankin et al. |
| 2014/0276811 A1 | 9/2014 | Koblish et al. |
| 2014/0288548 A1 | 9/2014 | Kim et al. |
| 2014/0330150 A1 | 11/2014 | Thakur et al. |
| 2014/0336518 A1 | 11/2014 | Shuros et al. |
| 2014/0350694 A1 | 11/2014 | Behan |
| 2014/0358137 A1 | 12/2014 | Hu |
| 2014/0364715 A1 | 12/2014 | Hauck |
| 2014/0364843 A1 | 12/2014 | Paul et al. |
| 2014/0364848 A1 | 12/2014 | Heimbecher et al. |
| 2014/0379093 A1 | 12/2014 | Durgin |
| 2015/0005624 A1 | 1/2015 | Hauck et al. |
| 2015/0011995 A1 | 1/2015 | Avitall et al. |
| 2015/0018813 A1 | 1/2015 | Gliner |
| 2015/0133914 A1 | 5/2015 | Koblish |
| 2015/0133920 A1 | 5/2015 | Rankin et al. |
| 2015/0148796 A1 | 5/2015 | Bencini |
| 2015/0164356 A1 | 6/2015 | Merschon et al. |
| 2015/0224326 A1 | 8/2015 | Toth et al. |
| 2015/0254419 A1 | 9/2015 | Laughner et al. |
| 2015/0265341 A1 | 9/2015 | Koblish |
| 2015/0265348 A1 | 9/2015 | Avitall et al. |
| 2015/0342672 A1 | 12/2015 | Bencini et al. |
| 2015/0374252 A1 | 12/2015 | De et al. |
| 2015/0374436 A1 | 12/2015 | Subramaniam et al. |
| 2016/0008065 A1 | 1/2016 | Gliner et al. |
| 2016/0089256 A1 | 3/2016 | Belhe et al. |
| 2016/0100884 A1 | 4/2016 | Fay et al. |
| 2016/0113582 A1 | 4/2016 | Altmann et al. |
| 2016/0113712 A1 | 4/2016 | Cheung et al. |
| 2016/0174865 A1 | 6/2016 | Stewart et al. |
| 2020/0138331 A1 | 5/2020 | Fay et al. |
| 2020/0222115 A1 | 7/2020 | Cheung et al. |

FOREIGN PATENT DOCUMENTS

| | | |
|---|---|---|
| CA | 2847846 A1 | 3/2013 |
| CA | 2848053 A1 | 3/2013 |
| CN | 1269708 A | 10/2000 |
| CN | 1455655 A | 11/2003 |
| CN | 1674836 A | 9/2005 |
| CN | 1942145 A | 4/2007 |
| CN | 101045016 A | 10/2007 |
| CN | 101879060 A | 11/2010 |
| CN | 102271607 A | 12/2011 |
| CN | 102573966 A | 7/2012 |
| CN | 102573986 A | 7/2012 |
| CN | 103251451 A | 8/2013 |
| CN | 103917185 A | 7/2014 |
| CN | 103987336 A | 8/2014 |
| CN | 104039257 A | 9/2014 |
| CN | 104244810 A | 12/2014 |
| CN | 104254368 A | 12/2014 |
| CN | 104619259 A | 5/2015 |
| CN | 104640513 A | 5/2015 |
| CN | 104661609 A | 5/2015 |
| EP | 1502542 A1 | 2/2005 |
| EP | 1547537 A1 | 6/2005 |
| EP | 0985423 B1 | 4/2006 |
| EP | 1343427 B1 | 7/2006 |
| EP | 1717601 A2 | 11/2006 |
| EP | 1935332 A2 | 6/2008 |
| EP | 1009303 B1 | 6/2009 |
| EP | 1343426 B1 | 10/2012 |
| EP | 2574278 A2 | 4/2013 |
| EP | 2755587 A2 | 7/2014 |
| EP | 2755588 A1 | 7/2014 |
| EP | 2136702 B1 | 7/2015 |
| EP | 2897545 A1 | 7/2015 |
| JP | 06-507797 A | 9/1994 |
| JP | 07-100214 A | 4/1995 |
| JP | 08-038501 A | 2/1996 |
| JP | 09-140803 A | 6/1997 |
| JP | 2000-000242 A | 1/2000 |
| JP | 2000-083918 A | 3/2000 |
| JP | 2000-504242 A | 4/2000 |
| JP | 2002-528039 A | 8/2002 |
| JP | 2003-504090 A | 2/2003 |
| JP | 2004-503335 A | 2/2004 |
| JP | 2005-500127 A | 1/2005 |
| JP | 2006-239414 A | 9/2006 |
| JP | 2007-513684 A | 5/2007 |
| JP | 2007-513685 A | 5/2007 |
| JP | 2007-163559 A | 6/2007 |
| JP | 2007-244857 A | 9/2007 |
| JP | 2008-080152 A | 4/2008 |
| JP | 2009-518150 A | 5/2009 |
| JP | 2009-142653 A | 7/2009 |
| JP | 2010-522623 A | 7/2010 |
| JP | 2011-142995 A | 7/2011 |
| JP | 2011-525842 A | 9/2011 |
| JP | 2012-531967 A | 12/2012 |

(56) References Cited

FOREIGN PATENT DOCUMENTS

| | | |
|---|---|---|
| JP | 5336465 B2 | 11/2013 |
| JP | 2014-012174 A | 1/2014 |
| JP | 2014-531244 A | 11/2014 |
| JP | 2015-501162 A | 1/2015 |
| JP | 2015-509027 A | 3/2015 |
| KR | 10-2010-0021401 A | 2/2010 |
| KR | 10-1490374 B1 | 2/2015 |
| WO | 92/21278 A1 | 12/1992 |
| WO | 94/13358 A1 | 6/1994 |
| WO | 96/04860 A1 | 2/1996 |
| WO | 97/25916 A1 | 7/1997 |
| WO | 97/25917 A1 | 7/1997 |
| WO | 97/36541 A1 | 10/1997 |
| WO | 97/45156 A2 | 12/1997 |
| WO | 99/02096 A1 | 1/1999 |
| WO | 98/58681 A3 | 3/1999 |
| WO | 99/09879 A1 | 3/1999 |
| WO | 99/27862 A1 | 6/1999 |
| WO | 99/53853 A1 | 10/1999 |
| WO | 00/29062 A2 | 5/2000 |
| WO | 01/41664 A1 | 6/2001 |
| WO | 01/58372 A1 | 8/2001 |
| WO | 01/64145 A1 | 9/2001 |
| WO | 01/68173 A2 | 9/2001 |
| WO | 01/74252 A2 | 10/2001 |
| WO | 01/80755 A2 | 11/2001 |
| WO | 02/02234 A1 | 1/2002 |
| WO | 02/05868 A2 | 1/2002 |
| WO | 02/09599 A2 | 2/2002 |
| WO | 02/19934 A1 | 3/2002 |
| WO | 02/47569 A1 | 6/2002 |
| WO | 2002/102234 A2 | 12/2002 |
| WO | 03/39338 A2 | 5/2003 |
| WO | 2004/093703 A1 | 11/2004 |
| WO | 2007/079278 A1 | 7/2007 |
| WO | 2008/003058 A2 | 1/2008 |
| WO | 2008/046031 A2 | 4/2008 |
| WO | 2008/118992 A1 | 10/2008 |
| WO | 2009/032421 A2 | 3/2009 |
| WO | 2009/048824 A1 | 4/2009 |
| WO | 2009/048943 A1 | 4/2009 |
| WO | 2010/001595 A1 | 1/2010 |
| WO | 2010/054409 A1 | 5/2010 |
| WO | 2010/056771 A1 | 5/2010 |
| WO | 2010/082146 A1 | 7/2010 |
| WO | 2011/008444 A1 | 1/2011 |
| WO | 2011/024133 A1 | 3/2011 |
| WO | 2011/033421 A1 | 3/2011 |
| WO | 2011/089537 A1 | 7/2011 |
| WO | 2011/095937 A1 | 8/2011 |
| WO | 2011/101778 A1 | 8/2011 |
| WO | 2012/001595 A1 | 1/2012 |
| WO | 2012/049621 A1 | 4/2012 |
| WO | 2012/066430 A1 | 5/2012 |
| WO | 2012/135703 A2 | 10/2012 |
| WO | 2012/151301 A1 | 11/2012 |
| WO | 2012/161880 A1 | 11/2012 |
| WO | 2012/166239 A1 | 12/2012 |
| WO | 2013/040201 A2 | 3/2013 |
| WO | 2013/040297 A1 | 3/2013 |
| WO | 2013/101923 A1 | 7/2013 |
| WO | 2014/036439 A2 | 3/2014 |
| WO | 2014/047281 A1 | 3/2014 |
| WO | 2014/058375 A2 | 4/2014 |
| WO | 2014/072879 A2 | 5/2014 |
| WO | 2014/152575 A2 | 9/2014 |
| WO | 2015/138465 A1 | 9/2015 |
| WO | 2015/143061 A1 | 9/2015 |
| WO | 2015/183635 A1 | 12/2015 |

OTHER PUBLICATIONS

Extended European Search Report issued in EP Application No. 15174537.9, dated Mar. 2, 2016, 7 pages.
Extended European Search Report issued in EP18177491.0, dated Oct. 26, 2018, 10 pages.
Goldberg, S. Nahum et al., "Variables Affecting Proper System Grounding for Radiofrequency Ablation in an Animal Model", JVIR, vol. 11, No. 8, Sep. 2000, pp. 1069-1075.
Goldbert, S. Nahum et al., "Variables Affecting Proper System Grounding for Radiofrequency Ablation in an Animal Model", JVIR, vol. 11, No. 8, Sep. 2000, pp. 1069-1075.
Hayerkamp, W., et al. Coagulation of Ventricular Myocardium Using Radiofrequency Alternating Current: Bio-Physical Aspects and Experimental Findings. PACE, 12:187-195, Jan. 1989, Part II.
International Search Report and Written Opinion issued in PCT/US2008/058324, dated Aug. 18, 2008, 11 pages.
International Search Report and Written Opinion issued in PCT/US2012/031819, dated Sep. 27, 2012, 16 pages.
International Search Report and Written Opinion issued in PCT/US2012/055155, dated Mar. 11, 2013, 19 pages.
International Search Report and Written Opinion issued in PCT/US2012/055309, dated Nov. 19, 2012, 13 pages.
International Search Report and Written Opinion issued in PCT/US2012/072061, dated Mar. 21, 2013, 9 pages.
International Search Report and Written Opinion issued in PCT/US2013/020503, dated Mar. 20, 2013, 10 pages.
International Search Report and Written Opinion issued in PCT/US2013/021013, dated Apr. 5, 2013, 14 pages.
International Search Report and Written Opinion issued in PCT/US2013/056211, dated Jan. 20, 2014.
International Search Report and Written Opinion issued in PCT/US2013/058105, dated Nov. 22, 2013, 16 pages.
International Search Report and Written Opinion issued in PCT/US2013/060183, dated Jan. 27, 2014, 10 pages.
International Search Report and Written Opinion issued in PCT/US2013/060194, dated Jan. 29, 2014, 10 pages.
International Search Report and Written Opinion issued in PCT/US2013/060612, dated Feb. 28, 2014, 16 pages.
International Search Report and Written Opinion issued in PCT/US2014/027491, dated Sep. 23, 2014, 17 pages.
International Search Report and Written Opinion issued in PCT/US2015/021300, dated Jun. 9, 2015, 11 pages.
International Search Report and Written Opinion issued in PCT/US2015/031591, dated Aug. 17, 2015, 11 pages.
International Search Report and Written Opinion issued in PCT/US2015/055173, dated Jan. 18, 2016, 11 pages.
International Search Report and Written Opinion issued in PCT/US2015/057242, dated Jan. 15, 2016, 11 pages.
International Search Report and Written Opinion issued in PCT/US2015/066874, dated Apr. 1, 2016, 11 pages.
International Search Report and Written Opinion issued in PCT/US2016/028006 dated Jul. 12, 2016, 12 pages.
International Search Report and Written Opinion received for PCT Patent Application No. PCT/US2010/023574, dated Jun. 18, 2010, 11 pages.
IPO First Examination Report issued in Patent Application No. 201717007706, dated Mar. 11, 2020, 7 pages.
Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.
Neufeld, Gordon R. et al., "Electrical Impedance Properties of the Body and the Problem of Alternate-site Burns During Electrosurgery", Medical Instrumentation, vol. 19, No. 2, Mar.-Apr. 1985, pp. 83-87.
Partial European Search Report issued in EP Application 18177491.0, dated Jul. 16, 2018, 11 pages.
Partial International Search Report issued in PCT/US2012/055155, dated Dec. 20, 2012, 7 pages.
Patriciu, A. et al., "Detecting Skin Burns Induced by Surface Electrodes", published in Engineering in Medicine and Biology Society, 2001, Proceedings of the 23rd Annual International Conference of the IEEE, vol. 3, pp. 3129-3131.
Pines, L. A., et al. Temperature-guided Radiofrequency Catheter Ablation of Closed-Chest Ventricular Myocardium with a Novel Thermistor-Tipped Catheter. American Heart Journal, 127(6):1614-1618, Jun. 1994.

(56) References Cited

OTHER PUBLICATIONS

Piorkowski, Christopher et al., "First in Human Validation of Impedance-Based Catheter Tip-to-Tissue Contact Assessment in the Left Atrium", Journal of Cardiovascular Electrophysiology, vol. 20, No. 12, Dec. 1, 2009, pp. 1366-1373.

Pires, L. A. et al. Temperature-guided Radiofrequency Catheter Ablation of Closed-Chest Ventricular Myocardium with a Novel Thermistor-Tipped Catheter American Heart Journal, 127(6): 1614-1618, Jun. 1994.

Price, Adam et al., "Novel Ablation Catheter Technology that Improves Mapping Resolution and Monitoring of Lesion Maturation", The Journal of Innovations in Cardiac Rhythm Management, vol. 3, 2002, pp. 599-609.

Price, Adam et al., "PO3-39 Pin Electrodes Improve Resolution: Enhanced Monitoring of Radiofrequency Lesions in the voltage and Frequency Domains", Heart Rhythm 2010, 31st Annual Scientific Sessions, May 12-15 in Denver Colorado.

Ring, E.R., et. Al. Catheter Ablation of the Ventricular Septum with Radiofrequency Energy. American Heart Journal, 117 (6): 1233-1240, Jun. 1989.

Steinke, Karin et al., "Dispersive Pad Site burns With Modern Radiofrequency Ablation Equipment", Surg Laparosc Endosc Percutan Tech, vol. 13, No. 6, Dec. 2003, pp. 366-371.

Supplemental European Search Report issued in EP Application 14740554 dated Sep. 26, 2016, 7 pages.

US Application entitled Pyloric Anchors and Methods for Intestinal Bypass Sleeves filed Mar. 3, 2016, U.S. Appl. No. 15/060,418.

Woodard et al., Probiotics Improve Outcomes After Roux-en-Y Gastric Bypass Surgery: A Prospective Randomized Trial, J Gastrointest Surg (2009) 13:1198-1204.

Zachary, J.M. et al., "PO4-86 Pin Electrodes Provide Enhanced Resolution Enabling titration of Radiofrequency Duration to Lesion Maturation", Heart Rhythm 2011, 32 Annual Scientific Sessions, May 4-7, San Francisco, CA.

\* cited by examiner

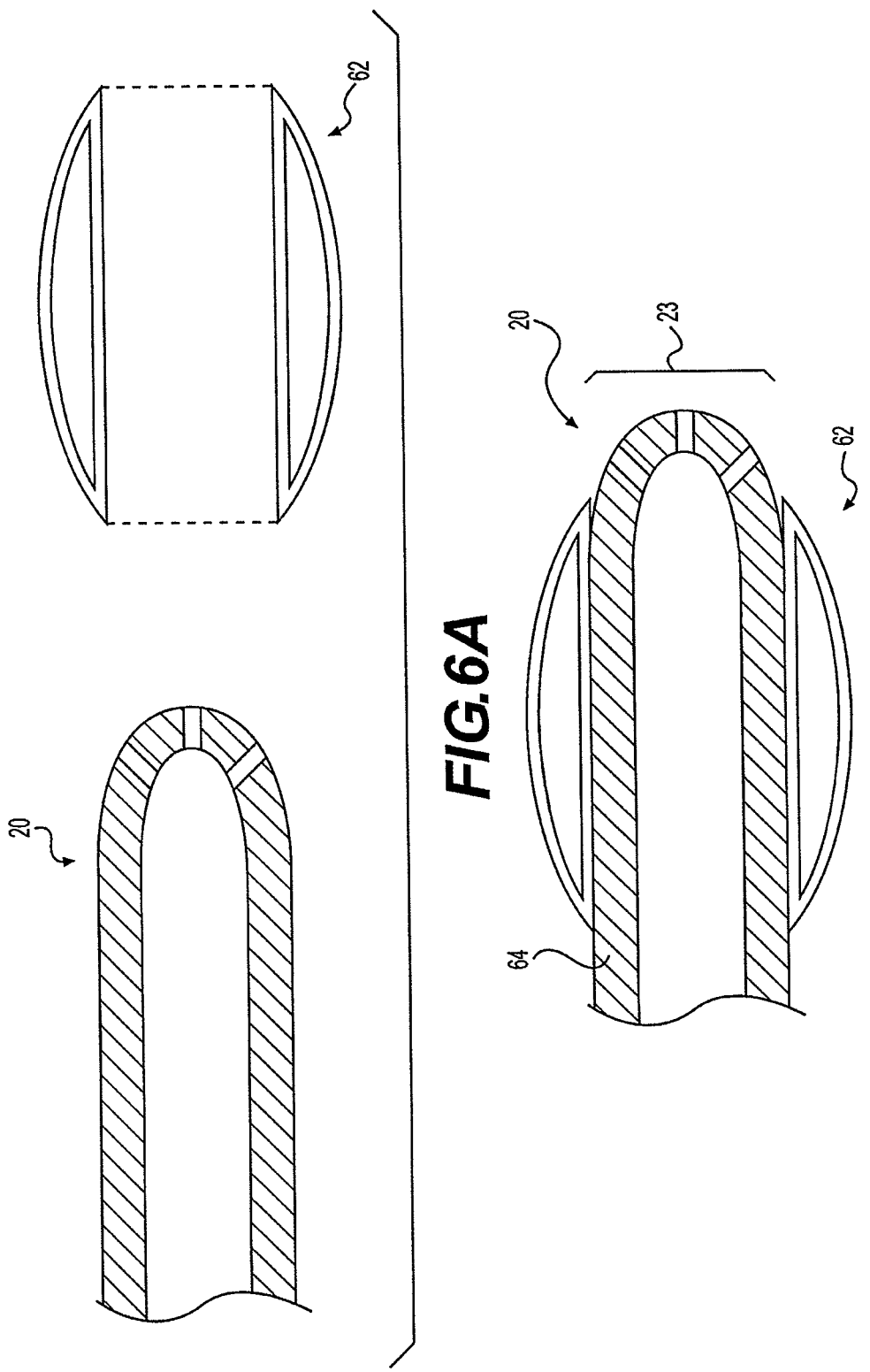

INSULATED ABLATION CATHETER DEVICES AND METHODS OF USE

CROSS-REFERENCE TO RELATED APPLICATIONS

The present application is a continuation of U.S. patent application Ser. No. 14/613,155, filed on Feb. 3, 2015, which is a continuation application of the U.S. patent application Ser. No. 12/702,396, filed on Feb. 9, 2010, now U.S. Pat. No. 8,945,117, which claims priority under 35 U.S.C. § 119(e) to U.S. Provisional Patent Application No. 61/151,709, which was filed on Feb. 11, 2009, the entirety of which are incorporated herein by reference.

FIELD

The present disclosure relates to the field of ablation and, more particularly, to insulated ablation catheter devices and methods of use.

BACKGROUND

Atrial fibrillation is a heart condition whereby abnormal electrical signals cause irregular heart contractions. One treatment for this condition includes open heart surgery and creating several lesions in the endocardium of the atria. These lesions can function to block aberrant electrical impulses, permitting an impulse originating from the sinus node to properly regulate heart contraction. However, because open heart surgery is highly invasive and requires a lengthy patient recovery period, alternate methods for making lesions are required. One alternative procedure uses ablation catheters.

Typically, an ablation catheter is advanced into the heart via the patient's blood vessels. When the catheter's electrodes are placed in the desired position within the heart chamber, radio frequency ("RF") energy is supplied to the catheter. Such RF energy ablates the tissue surrounding the ablation electrode, thereby creating a lesion in the endocardium.

Traditional ablation catheters included an elongated shaft with an ablation electrode mounted at the distal end of the shaft. Point or linear lesions could be formed with these catheters by manipulating the placement of the distal tip. However, creating suitable lesions using these catheters can be difficult because the tip electrode may overheat during ablation. Newer catheter designs mitigated these disadvantages by cooling the tip electrode during use, thereby minimizing the risk of overheating.

However cooled ablation catheters are limited in their ability to accurately determine the temperature of tissue surrounding the tip electrode. Temperature sensors of such catheters typically sense the temperature of the cooling fluid rather than tissue temperature. Accurate tissue temperature readings are desirable as they can provide a useful indication of tissue ablation. Accordingly, the present disclosure provides devices and methods for accurately determining tissue temperature that overcomes some of the disadvantages of current ablation technologies.

SUMMARY

Described herein are medical treatments for delivering ablative energy to target tissue while providing improved devices and methods for determining tissue temperature. In one aspect, an ablation catheter having an ablative electrode and an insulating chamber is disclosed. The catheter can include a pathway for providing cooling fluid to the ablative tip. Within the tip, cooling fluid can circulate in an open loop or closed loop configuration.

In one embodiment, a catheter device can be sized and shaped for vascular access. The catheter can include an elongate body extending between a proximal end and a distal end. Further, the elongate body can include at least one inner lumen configured to receive a fluid. The catheter can also include an ablation electrode configured to provide ablative energy, wherein the electrode can be located distally along the elongate body and can include a passageway fluidly connected to the lumen of the elongate body. The catheter can also include a sensor configured to provide a signal representative of temperature. In addition, the catheter can include an insulating chamber extending at least partially about the ablation electrode and configured to at least partially insulate the sensor from the ablation electrode.

Another aspect of the current disclosure is directed to a method for ablating tissue. The method includes the steps of providing an ablation electrode, wherein the ablation electrode can include a passageway fluidly connected to a lumen of an elongate body of a catheter device, an insulating chamber extending at least partially about the ablation electrode, and a temperature sensor at least partially insulated from the ablation electrode. The method can further include delivering fluid to the lumen to cool the ablation electrode, and delivering ablative energy to the ablation electrode.

Another aspect of the current disclosure is directed to an ablation electrode device configured to provide ablative energy to cardiac tissue. The electrode device can include a proximal section configured for attachment to an elongate body of a catheter device. The electrode device can further include a passageway configured to connect to a lumen of the elongate body, wherein the passageway can be configured to receive a fluid. Also included can be a sensor configured to provide a signal representative of a temperature of a region external to the ablation electrode. In addition, the electrode device can include an insulating chamber extending at least partially about the ablation electrode and configured to at least partially insulate the sensor.

Yet another aspect of the current disclosure is directed to a method of manufacturing an ablation electrode. The method can include providing a passageway configured to connect to a lumen of an elongate body of a catheter device, wherein the passageway can be configured to receive a fluid. The method can further include providing an insulating chamber extending at least partially about the ablation electrode. Also, the method can include attaching a sensor to the insulating chamber, wherein the sensor can be configured to provide a signal representative of a temperature of a region external to the ablation electrode.

It is to be understood that both the foregoing general description and the following detailed description are exemplary and are not restrictive of the present disclosure, as claimed. In addition, structures and features described with respect to one embodiment can similarly be applied to other embodiments.

BRIEF DESCRIPTION OF THE DRAWINGS

The accompanying drawings, which are incorporated in and constitute a part of this specification, provide illustrative embodiments of the present disclosure and, together with the description, serve to explain the disclosure's principles.

FIG. 6A illustrates a method of manufacturing an ablation electrode as described herein.

FIG. 6B illustrates a method of manufacturing an ablation electrode.

DETAILED DESCRIPTION

Disclosed herein are ablation catheters and methods of use. In general, the catheters include a flow path that provides cooling to a distal section of the catheter. The catheter can include an ablation electrode having irrigation apertures for delivery of a cooling fluid to the environment surrounding the electrode or to the surface of the electrode. In addition, the electrode can include an insulating chamber to at least partially thermally insulate a temperature sensor from other heat sources, such as, for example, the electrode or cooling fluid. The insulating chamber can improve the accuracy of sensing the temperature of the tissue or fluid surrounding the electrode.

Figure 1:
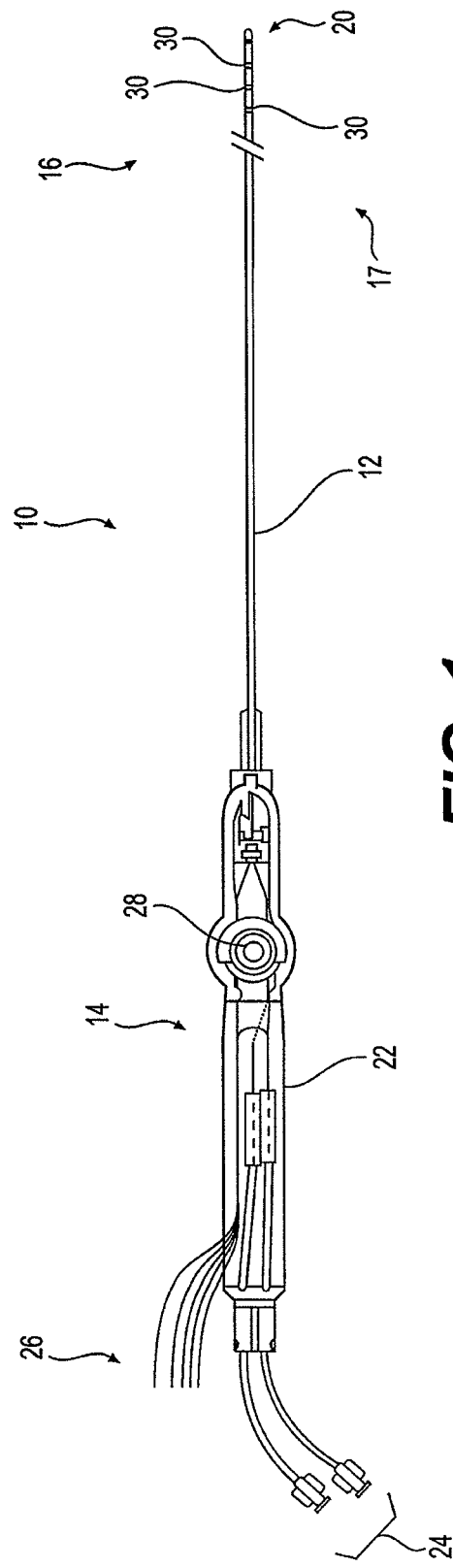
FIG. 1 illustrates a partially transparent view of one exemplary embodiment of an ablation catheter.

FIG. 1 provides a cut-away view of one exemplary embodiment of an ablation catheter device 10 for use with the electrode structure described herein. Catheter device 10 can include an elongate body 12 extending between a proximal section 14 and a distal section 16. Distal section 16 includes an ablation electrode 20, configured to deliver ablative energy to tissue as discussed in detail below.

In one aspect, proximal portion 14 of device 10 can include a handle 22 configured for use by a user. To permit operation of device 10, handle 22 can incorporate a variety of features to facilitate control of the catheter or the ablation process. For example, handle 22 can be configured to connect catheter device 10 to a source of fluid, a source of ablative energy, a temperature display, sensors, or control software or hardware. In particular, handle 22 can provide a source of cooling fluid for electrode 20 via one or more ports 24, configured to receive or expel fluid. In addition, device 10 can include mating elements 26 for receiving or transmitting energy to electrodes located distally along elongate body 12, such as, for example, electrode 20. One skilled in the art will appreciate that a variety of catheter handle configurations are contemplated depending on the features of the elongate body 12, ablation electrode 20, or the intended use of catheter device 10.

In some embodiments, catheter device 10 can be articulating. For example, catheter device 10 can include an articulating section 17, located distally along elongate body 12. Specifically, distal section 16 can be deflected or bent in one or more directions. Articulation can provide one or more degrees of freedom and permit up/down or left/right movement of elongate body 12. One skilled in the art will understand that catheter 10 can include a variety of features associated with conventional articulating catheter devices.

Articulating section 17 can be controlled via a proximally located control mechanism 28. Control mechanism 28 can be mounted on handle 22 and can direct movement of distal section 16 of elongate body 12. Such movement of elongate body 12 can facilitate insertion of catheter device 10 through a body lumen, such as, for example, vasculature. Control mechanism 28 can also manipulate distal section 16 to place electrode 20 at a target tissue location.

Elongate body 12 can be defined by a flexible cylindrical structure extending between handle 22 and distal section 16. In one embodiment, body 12 can house at least one lumen configured to receive a fluid. Such fluid can be transferred to electrode 20 for cooling purposes. In addition, body 12 can house electrical conductors, such as, for example, wires for transmitting sensed signals or ablation energy. Also, articulation mechanisms, such as, for example, control wires, can extend within body 12 to articulation section 17 to permit movement of catheter device 10. One skilled in the art will appreciate that body 12 can include a variety of structures shaped and sized to pass through a body cavity, such as, for example, a vascular lumen.

Where catheter device 10 includes articulating section 17, control wires (e.g., push/pull wires) can be configured to mate with distal section 16 of elongate body 12. For example, a reinforcing or anchor member (not shown) could be positioned within distal section 16. One or more control wires could mate with the reinforcing member to anchor the distal end of the control wire. However, such wires can alternatively, or additionally, be fixed at a more proximal location of device 10.

Distal section 16 of catheter device 10 can include at least one electrode for delivering ablation energy, sensing physiological signals, or functioning as a return electrode. In one aspect, one or more ring electrodes 30 can be located distally along elongate body 12. Ring electrodes 30 can, for example, permit sensing or mapping of cardiac signals. FIG. 1 illustrates three ring electrodes 30 within distal section 16 and positioned proximally from electrode 20. Various ring electrodes 30 or electrode 20 can be used to sense physiological signals. Mapping is usually accomplished using a pair of electrodes, including, for example, electrode 20.

In addition to sensing, distal section 16 of device 10 can be configured to deliver ablation energy using bipolar or monopolar signals. For example, radio frequency (RF), microwave, or other ablative energy can be delivered via one or more electrodes, such as, for example, ablation electrode 20. One or more ring electrodes 30, or a separate ground pad, can function as a return electrode.

FIGS. 2 to 5 illustrate various exemplary embodiments of ablation electrode 20. In one aspect, electrode 20 is configured to deliver RF energy to target tissue. To reduce coagulum formation, electrode 20 can include a flow path, indicated by arrow 21, for regulating the temperature of electrode 20. A build up of biological materials on the outer surface of electrode 20 or in the area surrounding electrode 20 can result in less effective energy transfer to the tissue. This effect can be seen as a rise in impedance and a corresponding increase in tissue heating or charring immediately adjacent to ablation electrode 20. Cooling of electrode 20 can permit more efficient energy transfer to tissue and allow larger lesion sizes. For example, cooling fluid moving through electrode 20 can absorb heat to reduce the electrode's temperature.

In some embodiments, a flow path can direct fluid through electrode 20 to the outer surface of electrode 20. The fluid can function as a conduit to transmit RF energy to tissue. Also, movement of fluid around electrode 20 while device 10 is in contact with tissue can reduce impedance rise as energy is delivered to the tissue. In some situations, the movement of the fluid can sweep biological material, such as, for example, blood and tissue, away from electrode 20 to reduce the build-up of embolic material.

Catheter device 10 also includes at least one insulating chamber configured to at least partially reduce heat transfer associated with conventional ablation catheters. Previously, temperature readings from the distal tip of ablation catheters could be affected by the other heat sources. Specifically, the temperature of the cooling fluid could modify the temperature sensed at a distal tip. Also, ablation electrodes can increase in temperature during an ablative procedure, again reducing the temperature measurement's accuracy.

In some embodiments, an insulating chamber 62 is configured to at least partially insulate a temperature sensor 46 from distal section 16 of catheter device 10. Insulating chamber 62 can contain air, other fluid, or a solid material. Such insulating substances are designed to reduce energy flow between temperature sensor 46 and other components of distal section 16. Temperature sensor 46 may then be configured to accurately sense the temperature of the environment or region surrounding distal section 16. Such temperature information can provide a better indication of tissue ablation.

Figure 2:
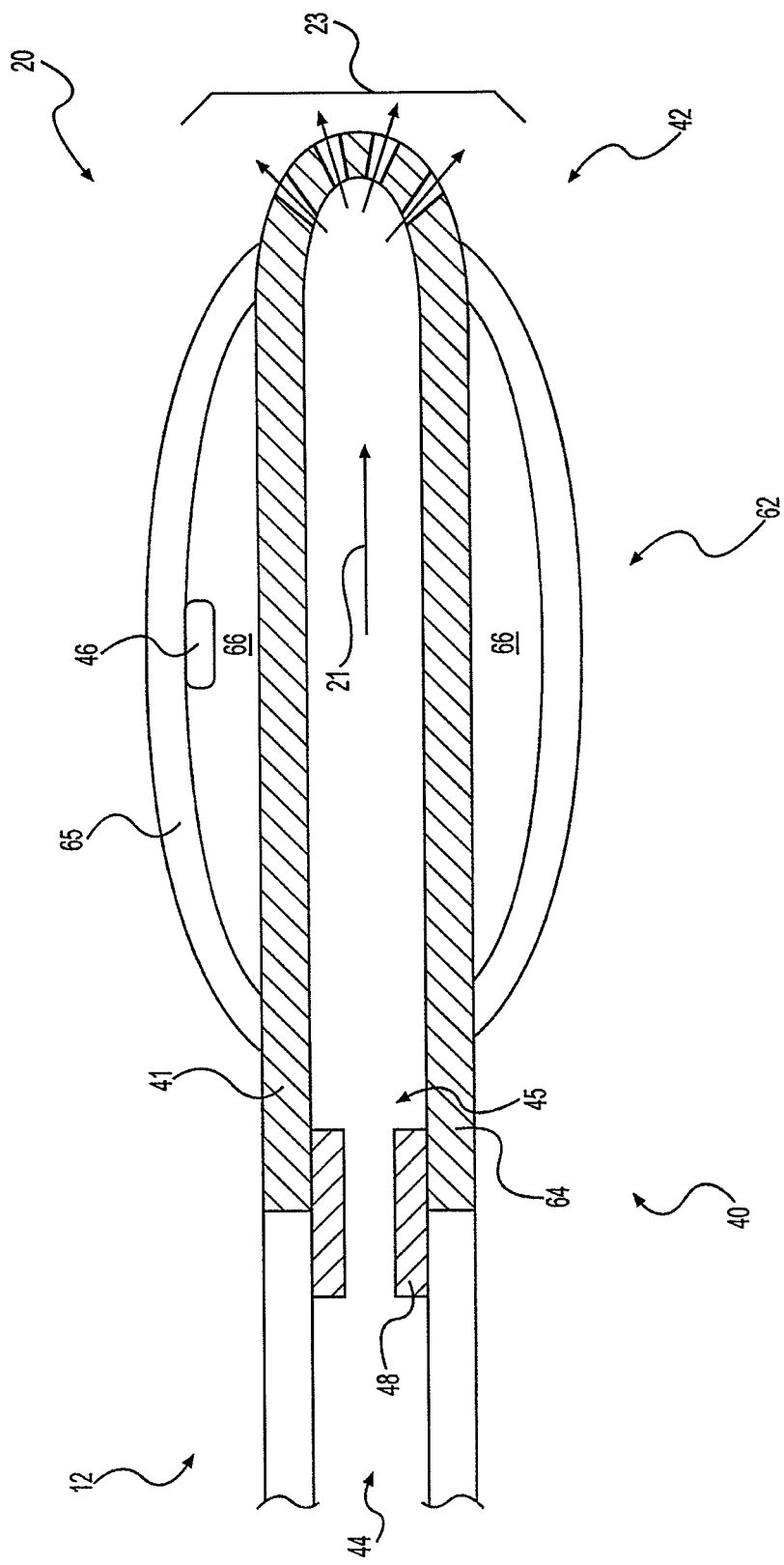
FIG. 2 illustrates a cross-sectional view of one embodiment of an ablation electrode described herein.

FIG. 2 illustrates one embodiment of electrode 20 having a proximal end 40 and a distal end 42, wherein proximal end 40 can be configured to mate with elongate body 12. In one embodiment, a connecting member 48 can be configured to connect electrode 20 and elongate body 12. For example, connecting member 48 could be a generally cylindrical structure configured to mate with an inner surface of body 12 and electrode 20. Alternatively, electrode 20 and body 12 could mate via an overlapping connection (not shown), whereby a portion of electrode 20 or body 12 could be positioned within or about a portion of the other structure. One skilled in the art will appreciate that a variety of mating mechanisms could be used, including frictional, mechanical, or adhesive engagements. In other embodiments, a sheath could extend about part of elongate body 12 or electrode 20.

In one embodiment, electrode 20 includes a body 41 configured to provide ablation energy to tissue. Body 41 can be constructed of a single unibody structure or of multiple segments of similar or different materials. Irrespective of its construction, body 41 can be formed of a variety of electrically and/or thermally conductive materials including, for example, platinum, iridium, stainless steel, gold, plated brass, and combinations thereof. In another aspect, body 41 could be an electrically conductive material, but not necessarily a thermally conductive material.

Electrode 20 can be configured to operate with various lumens, wires, or control mechanisms. In particular, proximal end 40 of electrode 20 can be configured to mate with various lumens, wires, or control mechanisms extending through body 12. For example, a passageway 45 within electrode 20 could be configured to receive fluid. In some embodiments, passageway 45 can be in fluid communication with a lumen 44 associated with elongate body 12. Fluid may flow into catheter device 10 via ports 24 (as shown in FIG. 1), through lumen 44 and into passageway 45. In other embodiments, one or more lumens may be fluidly connected with one or more passageways in electrode 20.

In some embodiments, one or more apertures 23 may be configured to direct a fluid from passageway 45 to a region surrounding electrode 20. As illustrated in FIG. 2, four apertures 23 are shown although a different number of apertures 23 may also be used. As discussed below with respect to FIG. 3, electrode 20 may include no apertures.

In some embodiments, catheter device 10 can include insulating chamber 62 located distally along device 10. In particular, insulating chamber 62 can be positioned proximal to at least a portion of electrode 20 or adjacent to distal end 42 of electrode 20. Further, insulating chamber 62 can at least partially extend, or extend substantially, about electrode 20. By at least partially surrounding an outer surface of electrode 20, insulating chamber 62 can provide at least some insulation from energy originating from distal section 16. For example, insulating chamber 62 can function to reduce heat transfer to a distally located temperature sensor 46, such as, for example, a thermocouple or thermistor. In some embodiments, sensor 46 may be located within insulating chamber 62.

Insulating chamber 62 can be configured to form various shapes. For example, insulating chamber 62 could be a generally cylindrical shape, extending in a longitudinal direction parallel to a longitudinal axis of electrode 20. Such a curvilinear form may also include linear or curvilinear sections. In particular, insulating chamber 62 could be a "peanut" shape, including generally bulbous distal and proximal sections and a smaller section between. Insulating chamber 62 could also be generally pear shaped or generally spherical.

In one aspect, insulating chamber 62 can include a sidewall 65. Sidewall 65 could be constructed of any suitable material, such as, for example, an alloy, a polymer, a ceramic, or combinations thereof. Sidewall 65 may be mated with a sidewall 64 of electrode body 41 via welding, heat sealing, friction fit, or other methods known in the art. Sidewall 65 may also be at least partially insulated from sidewall 64 to at least partially reduce heat transfer from sidewall 64 to sidewall 65. For example, sidewall 65 may be bonded to sidewall 64 using an insulative glue or other suitable adhesive. Also, sidewall 64 and/or sidewall 65 may be formed from or bonded with, in part or in whole, an insulative material.

Insulating chamber 62 can include an enclosed volume 66 that provides at least a partial insulative function. In particular, volume 66 can partially insulate sensor 46 from one or more heat sources. In some embodiments, volume 66 may be defined by a region enclosed by sidewalls 64 and 65. Also, volume 66 could be at least partially filled with various fluids or solids. For example, volume 66 could be filled with air, nitrogen, water, saline solution, foam, polymer, or ceramic material. Such substances may have low thermal and/or electrical conductivity.

Figure 3:
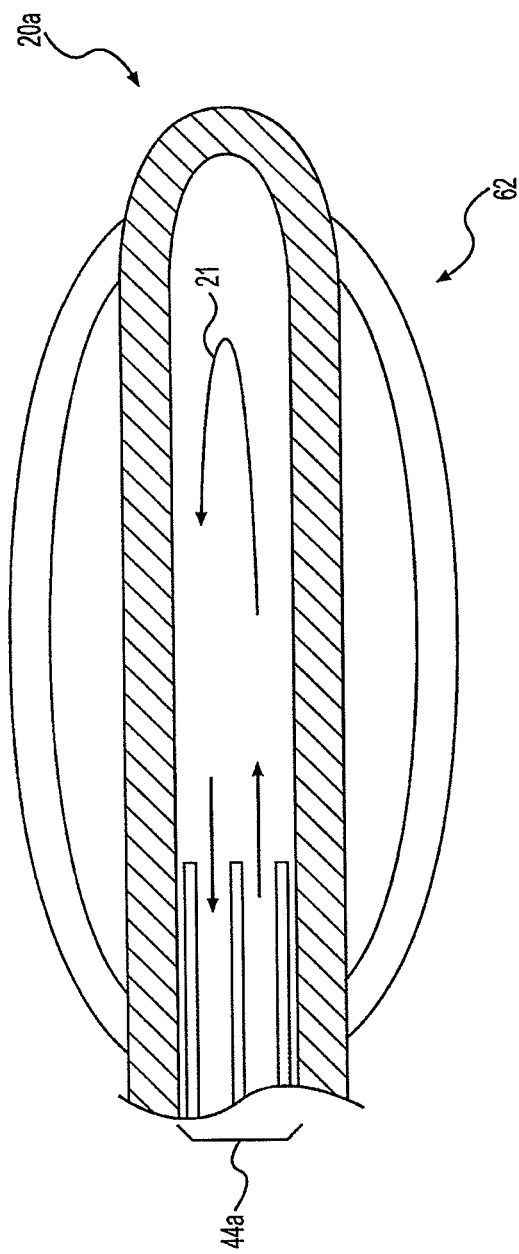
FIG. 3 illustrates a cross-sectional view of another embodiment of an ablation electrode.

As illustrated in FIG. 3, electrode 20a may operate with a closed loop fluid circulation system. Specifically, fluid flow 21 may enter and exit electrode 20a via two or more lumens 44a. While electrode 20a contains no apertures, fluid can be expelled from electrode 20a via a lumen 44a configured to receive fluid flow 21 and transfer fluid away from electrode 20a.

Figure 4:
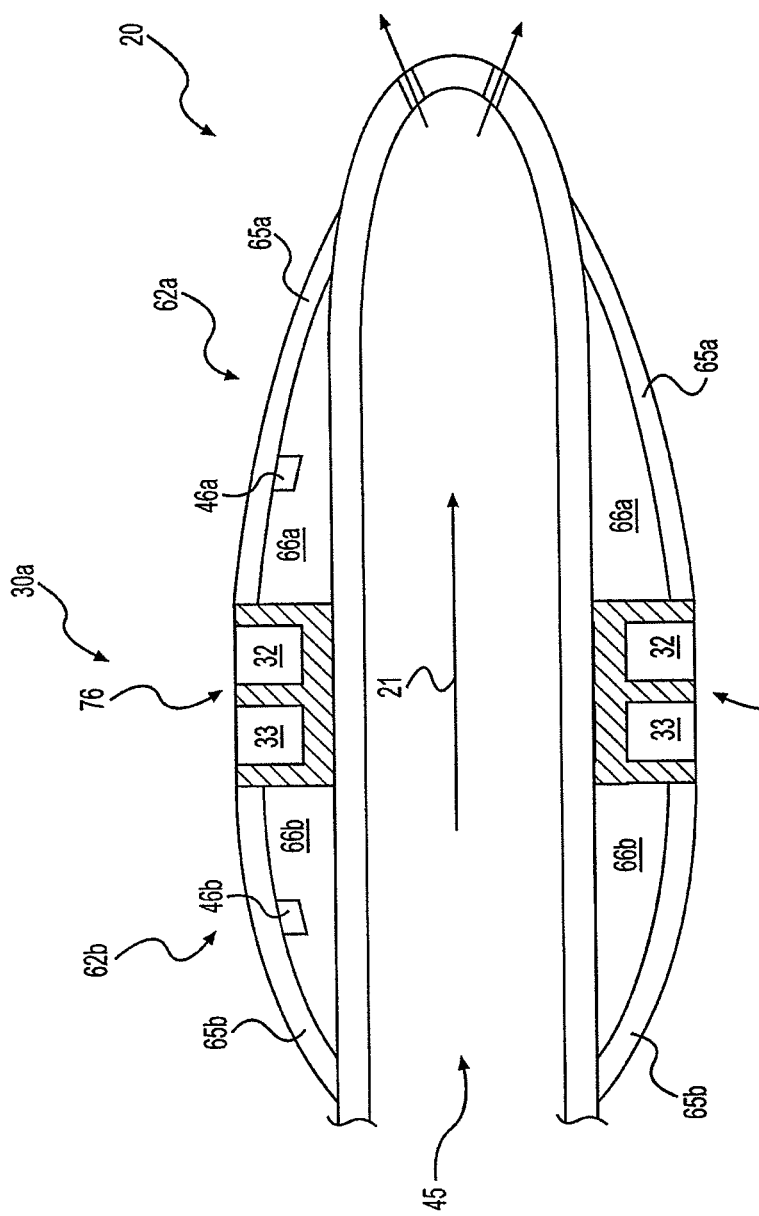
FIG. 4 illustrates a cross-sectional view of another embodiment of an ablation electrode.

In some embodiments, electrode 20 could include two or more insulating chambers. FIG. 4 illustrates one embodiment of electrode 20 having a first insulating chamber 62a and a second insulating chamber 62b. As described above, insulating chambers 62a, 62b may include one or more side walls 65a, 65b that may generally extend at least partially about electrode 20. As previously described, insulating chambers 62a, 62b can be variously shaped and sized. Also, insulating chambers 62a, 62b can include volumes 66a, 66b that may be filled with various or different insulating materials. Chambers 62a, 62b could be differently configured, and may include multiple temperature sensors 46a, 46b.

FIG. 4 illustrates an embodiment of electrode 20 having one or more ring electrodes 30a. Specifically, ring electrodes 30a includes a distal ring electrode 32 and a proximal ring electrode 33. Other embodiments of electrode 20 could include more or less ring electrodes 30a configured to sense a physiological signal.

In some embodiments, ring electrodes 30a could extend at least partially about electrode 20. Also, ring electrodes 32, 33 may be separated by an insulating material 76. Insulating material 76 could separate one or more ring electrodes from each other, one or more insulating chambers 62a, 62b, or electrode 20. Insulating material 76 may be different to insulating material contained with volumes 66a, 66b. In some embodiments, the insulating materials could be similar.

Figure 5:
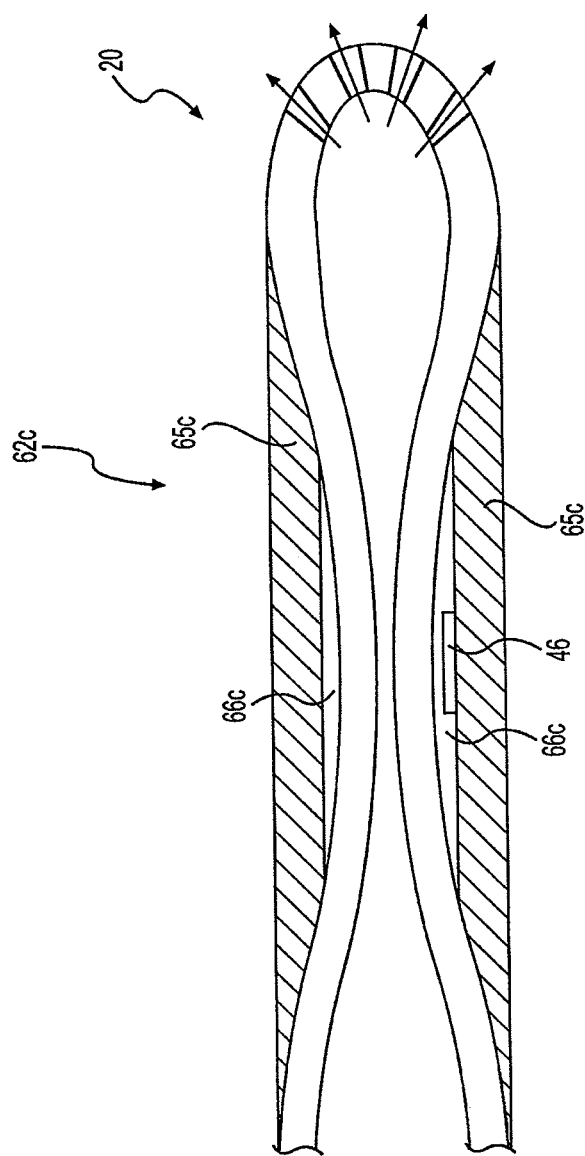
FIG. 5 illustrates a cross-sectional view of another embodiment of an ablation electrode.

FIG. 5 illustrates another embodiment of electrode 20. As shown, electrode 20 and insulating chamber 62c can be configured to form an outer structure having a substantially similar cross-section along its longitudinal axis. Specifically, electrode 20 can include a concave region configured to provide a concave sidewall of volume 66c. Another sidewall of volume 66c can be provided by a generally linear sidewall 65c, such that insulating chamber 62c can have an outer diameter similar to the outer diameter of electrode 20 at its distal end.

As illustrated in FIGS. 2, 4 and 5, temperature sensor 46 can be positioned within insulating chamber 62. Electrically conductive wires can extend through elongate body 12 or electrode 20 to deliver energy or to permit communication with sensor 46. In other embodiments, sensor 46 can be positioned about insulating chamber 62. In one aspect, the limited thermal conductivity of insulating chamber 62 facilitates accurate temperature sensing of the region surrounding electrode 20. For example, insulating chamber 62 can provide sufficient thermal insulation such that a temperature of the surrounding region is approximately equal to the temperature of sidewall 65 or insulating chamber 62.

Various methods may be used to manufacture ablation electrode 20 or insulating chamber 62. For example, as shown in FIG. 6A, both electrode 20 and insulating chamber 62 can be preformed as two separate components. All or a portion of insulating chamber 62 can be defined by a separate structure and can be configured to mate with part of electrode 20. As illustrated in FIG. 68, both components may then be combined to form a complete electrode assembly. Alternatively, as shown in FIGS. 2 to 5, one or more sidewalls 65 may be attached to sidewalls 64 to form insulating chambers 62. Such attachment can include welding, soldering, gluing, or other suitable methods.

The concept of an electrode and an insulating chamber may be discussed as separate elements for the sake of convenience or clarity, but such a description does not limit electrode 20, as described or claimed, to a configuration in which the insulating chamber 62 is a distinct structure mated with electrode 20. In addition, the outer surface of insulating chamber 62 can define a portion of the outer surface of electrode 20. For example, sidewall 65 can define the outer surface of electrode 20. Also, part of insulating chamber 62 could be manufactured from material similar or different to a material used to manufacture electrode 20. For example, sidewall 65 could be similar or different material to sidewall 64.

Irrigation apertures 23 can be formed in a variety of ways. In one aspect, channels can be drilled through sidewall 64. While a macroporous electrode 20 is illustrated in the figures, microporous structures are also contemplated. For example, the sidewall 64 could be formed from sintered material having a porosity which allows cooling fluid flow therethrough. One skilled in the art will appreciate that a variety of conventional macro or microporous catheter materials can be utilized to form electrode 20.

One skilled in the art will appreciate that the shape of electrode 20 can be varied according to the use of device 10. For example, another embodiment of ablation electrode 20 could include a blunt distal end. Other embodiments of the present disclosure will be apparent to those skilled in the art from consideration and practice of the specification. It is intended that the specification and examples be considered as exemplary only, with a true scope and spirit of the present disclosure being indicated by the following claims.

What is claimed is:

1. A catheter device configured for vascular access, comprising:
    an elongate body extending between a proximal end and a distal end, wherein the elongate body includes a lumen configured to receive a fluid;
    an ablation electrode configured to provide ablative energy, wherein the ablation electrode is coupled to the distal end of the elongate body and has an outer surface defining a distal region and a concave region extending circumferentially around the electrode, and wherein the concave region has an outer diameter that is smaller than an outer diameter of the distal region;
    an insulating chamber extending around the outer surface of the concave region of the ablation electrode, wherein the insulating chamber has an outer wall having an outer diameter such that the ablation electrode and insulating chamber are substantially isodiametric and further wherein the insulating chamber defines an area between the outer wall and the concave region of the ablation electrode; and
    a temperature sensor disposed within the area.

2. The device of claim 1, wherein the temperature sensor is coupled to a sidewall of the insulating chamber.

3. The device of claim 1, wherein the insulating chamber is configured to at least partially insulate the temperature sensor from the ablation electrode, the insulating chamber defining a fixed volume and attached to the ablation electrode using an insulative material, wherein the sensor is located on an inner surface of the insulating chamber, spaced apart from an outer surface of the ablation electrode.

4. The device of claim 1, wherein the insulating chamber includes at least one material selected from the group of: a fluid material and a solid material.

5. The device of claim 4, wherein the fluid includes at least one fluid selected from the group of: air, nitrogen, water, and a saline solution.

6. The device of claim 4, wherein the solid material includes at least one solid selected from the group of: a foam, a polymer, and a ceramic material.

7. A method for ablating tissue using a catheter device including an ablation electrode and an insulating chamber, the method comprising:
    positioning the ablation electrode adjacent to tissue to be ablated, wherein the ablation electrode has a concave region extending circumferentially around the electrode and a distal region, wherein the concave region has an outer diameter that is smaller than an outer diameter of the distal region, and wherein the insulating chamber extends around an outer surface of the concave region of the ablation electrode such that the ablation electrode and insulating chamber are substantially isodiametric and further wherein the insulating chamber defines an area between the outer wall and the concave region of the ablation electrode, the area housing a temperature sensor;

delivering fluid to the lumen to cool the ablation electrode; and delivering ablative energy to the ablation electrode.

8. The method of claim 7, wherein the temperature sensor is disposed on a sidewall of the insulating chamber.

9. An ablation electrode device configured to provide ablative energy to cardiac tissue, comprising:
- an ablation electrode comprising a proximal section configured for attachment to an elongate body of a catheter device, wherein the ablation electrode has a concave region extending circumferentially around the electrode and a distal region, and wherein the concave region has an outer diameter that is smaller than an outer diameter of the distal region;
- a passageway configured to connect to a lumen of the elongate body, wherein the passageway is configured to receive a fluid; and
- an insulating chamber extending around an outer surface of the concave region of the ablation electrode, and wherein the insulating chamber has an outer diameter such that the ablation electrode and insulating chamber are substantially isodiametric and further wherein the insulating chamber defines an area between the outer wall and the concave region of the ablation electrode; and
- a temperature sensor disposed within the area.

10. The ablation electrode device of claim 9, wherein proximal and distal ends of the ablation electrode extend beyond the insulating chamber.

11. The ablation electrode device of claim 9, wherein the insulating chamber is attached to the ablation electrode using an insulative material.

12. The ablation electrode device of claim 9, wherein the temperature sensor is disposed on a sidewall of the insulating chamber.

13. The ablation electrode device of claim 9, wherein the sensor is disposed on an inner surface of the insulating chamber and spaced apart from the outer surface of the ablation electrode.

14. The electrode device of claim 9, wherein the insulating chamber includes at least one material selected from the group of: a fluid and a solid material.

\* \* \* \* \*